US010052093B2

(12) United States Patent
Housman

(10) Patent No.: US 10,052,093 B2
(45) Date of Patent: Aug. 21, 2018

(54) BLENDED SHAFT DRIVE

(71) Applicant: SMITH & NEPHEW, INC., Memphis, TN (US)

(72) Inventor: Mark Edwin Housman, North Attleborough, MA (US)

(73) Assignee: Smith & Nephew, Inc., Memphis, TN (US)

( * ) Notice: Subject to any disclaimer, the term of this patent is extended or adjusted under 35 U.S.C. 154(b) by 198 days.

(21) Appl. No.: 14/739,245

(22) Filed: Jun. 15, 2015

(65) Prior Publication Data

US 2016/0038136 A1 Feb. 11, 2016

Related U.S. Application Data

(63) Continuation of application No. 13/276,920, filed on Oct. 19, 2011, now Pat. No. 9,084,595.

(51) Int. Cl.
*A61B 17/04* (2006.01)
*A61B 17/88* (2006.01)
(Continued)

(52) U.S. Cl.
CPC ...... *A61B 17/0401* (2013.01); *A61B 17/8615* (2013.01); *A61B 17/888* (2013.01); *A61F 2/0811* (2013.01); *A61B 2017/00407* (2013.01); *A61B 2017/0403* (2013.01); *A61B 2017/0409* (2013.01); *A61B 2017/0414* (2013.01); *A61B 2017/0445* (2013.01);
(Continued)

(58) Field of Classification Search
CPC ........ A61B 2017/0409; A61B 17/8615; A61B 17/0401

USPC .......... 606/232; 411/395, 410; 80/436, 438, 80/439, 441, 460, 461
See application file for complete search history.

(56) References Cited

U.S. PATENT DOCUMENTS 3,586,080 A 6/1971 Slany
4,269,246 A * 5/1981 Larson ............... A61B 17/8615
411/403

(Continued)

FOREIGN PATENT DOCUMENTS

EP 1101459 A2 5/2001

OTHER PUBLICATIONS

International Search Report for PCT/US2012/059780 dated Feb. 18, 2013.
(Continued)

*Primary Examiner* — Thomas McEvoy
(74) *Attorney, Agent, or Firm* — Burns & Levinson, LLP; Joseph M. Maraia

(57) ABSTRACT

A solid, monolithic shaft member has an engagement end. The engagement end has a proximal end a distal end. The proximal end has a first cross-sectional geometry, and the distal end has a second cross-sectional geometry. The first cross-sectional geometry of the proximal end is different from the second cross-sectional geometry of the distal end. The cross-sectional geometry of the distal end transitions to the a cross-sectional geometry of the proximal end along a longitudinal axis of the engagement end of the solid, monolithic shaft member. This transition provides a gradual, blending, continuously transitioning cross-sectional geometry along the entire length of the longitudinal axis of the engagement end of the solid, monolithic shaft member.

7 Claims, 9 Drawing Sheets

(51) Int. Cl.
  *A61B 17/86* (2006.01)
  *A61F 2/08* (2006.01)
  *A61B 17/00* (2006.01)
  *A61B 90/00* (2016.01)

(52) U.S. Cl.
  CPC . *A61B 2017/0453* (2013.01); *A61B 2090/031* (2016.02); *A61F 2002/0835* (2013.01); *A61F 2002/0852* (2013.01)

(56) References Cited

U.S. PATENT DOCUMENTS

| | | | |
|---|---|---|---|
| 4,827,811 | A | 5/1989 | Vickers |
| 5,139,499 | A | 8/1992 | Small et al. |
| 5,354,299 | A | 10/1994 | Coleman |
| 5,359,911 | A | 11/1994 | Gertzman et al. |
| 5,461,952 | A | 10/1995 | Goss |
| 6,016,727 | A | 1/2000 | Morgan |
| 6,019,022 | A * | 2/2000 | Dotson .......... B25B 15/00 7/165 |
| 6,045,300 | A * | 4/2000 | Antoun .......... B23B 27/10 407/11 |
| 7,188,554 | B2 | 3/2007 | Bayham |
| 7,325,470 | B2 | 2/2008 | Kay et al. |
| 7,846,167 | B2 | 12/2010 | Garcia |
| 2001/0041937 | A1 | 11/2001 | Rieser et al. |
| 2007/0270954 | A1 | 11/2007 | Wu |
| 2010/0251861 | A1 | 10/2010 | Sixto, Jr. et al. |
| 2011/0112576 | A1 | 5/2011 | Nguyen et al. |

OTHER PUBLICATIONS

International Preliminary Report on Patentability for PCT/US2012/059780 dated Apr. 22, 2014.

* cited by examiner

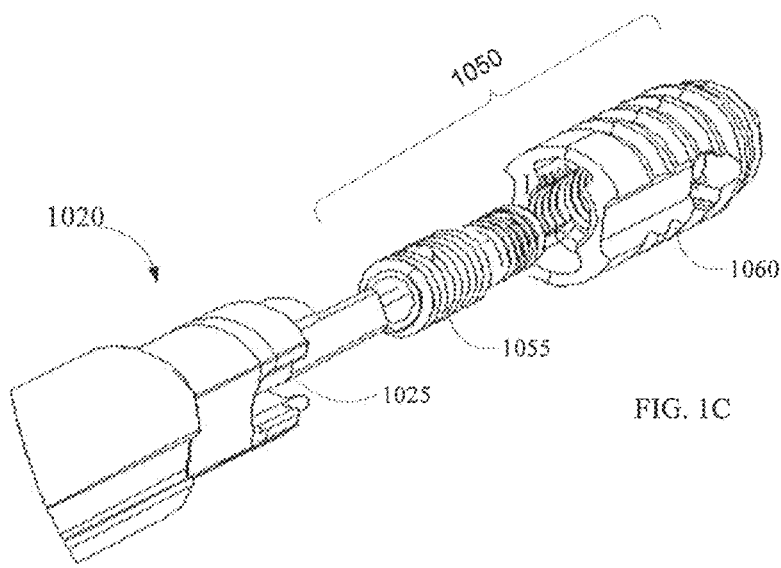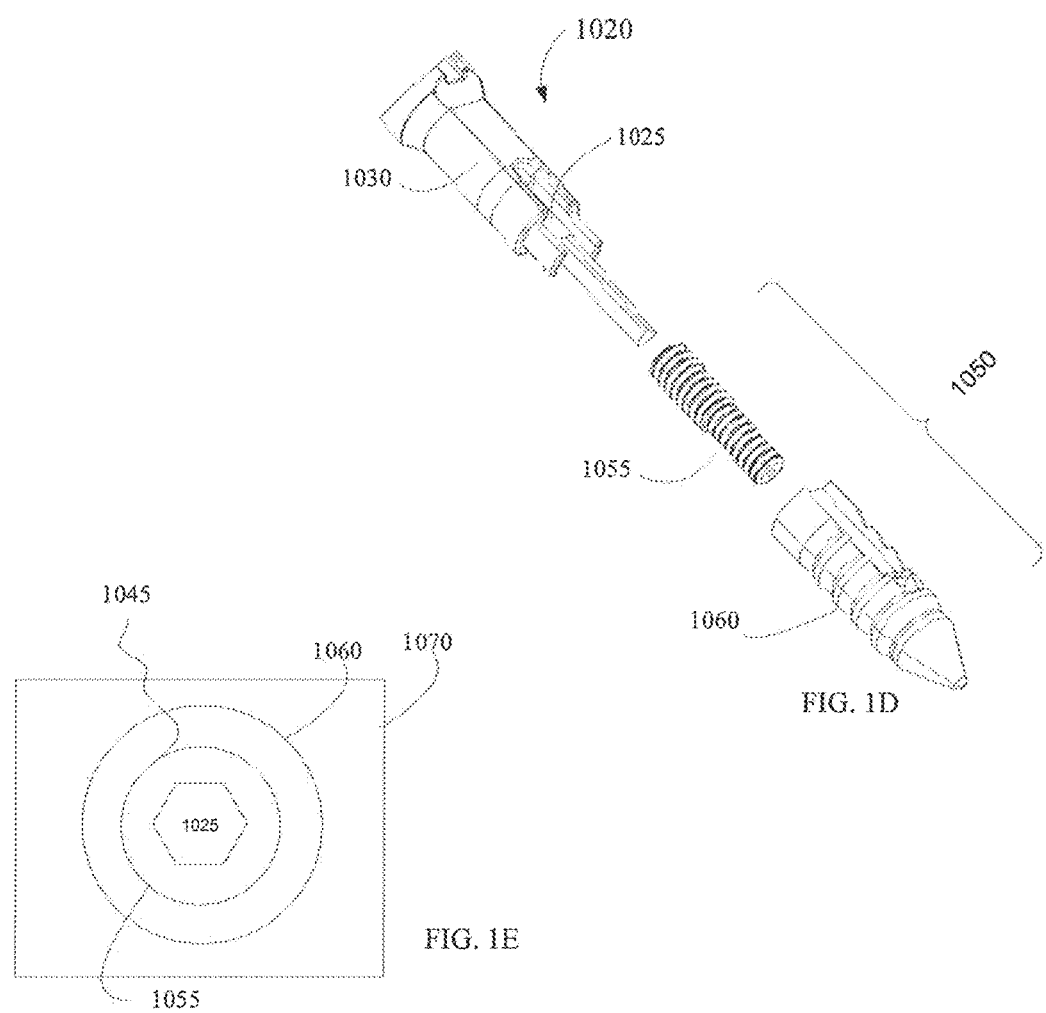

Midway

Distal

BLENDED SHAFT DRIVE

CROSS-REFERENCE TO RELATED APPLICATION(S)

This application is a continuation of U.S. patent application Ser. No. 13/276,920, filed on Oct. 19, 2011 and entitled "BLENDED SHAFT DRIVE," the entirety of which is hereby incorporated herein by reference.

BACKGROUND

Shaft drive tools, generally, have insufficient torque carrying capability and can fail under torsion loading. Specifically, shaft drive tools incorporate a drive feature that transitions rapidly to a base geometry (usually a cylinder), and this rapid transition in geometry creates a failure location at which stress risers accumulate and cause catastrophic failure under load. Occurrences of this type of failure are increasingly likely as drive tools are narrowed for the delivery of increasingly smaller diameter fasteners. A need therefore exists for an improved shaft drive.

SUMMARY

One approach provides an improved blended shaft delivery device. The delivery device includes a solid, monolithic shaft member. The shaft member has an engagement end. The engagement end has a proximal end and a distal end. The proximal end has a first cross-sectional geometry, and the distal end has a second cross-sectional geometry. The first cross-sectional geometry of the proximal end is different from the second cross-sectional geometry of the distal end. The cross-sectional geometry of the distal end transitions to the cross-sectional geometry of the proximal end along a longitudinal axis of the engagement end of the solid, monolithic shaft member. The transition provides a gradual, blending, continuously transitioning cross-sectional geometry along the entire length of the longitudinal axis of the engagement end of the solid, monolithic shaft member.

In some examples, the cross-sectional geometry of the distal end is in a shape of at least one of a triangle, a square, a rectangle, a hex, a circle, an ellipse, a cross, and a torx. In some examples, the cross-sectional geometry of the proximal end is in a shape of at least one of a triangle, a square, a rectangle, a hex, a circle, an ellipse, a cross, and a torx. In other examples, cross-sectional geometry of the distal end of the delivery device is in a shape of a polygon.

In some examples, the solid, monolithic shaft member has no abrupt transitions in cross-sectional geometries along the longitudinal axis, and the cross-sectional geometry of at least one of the proximal end or the distal end has a shape adapted to mate with a fastener cavity of substantially the same shape. In some examples, the fastener cavity provides a blending, continuously transitioning cross-sectional geometry along the longitudinal axis of the cavity adapted for receiving the blending, continuously transitioning cross-sectional geometry of the engagement end of the solid, monolithic shaft. In other examples, the fastener cavity includes at least two different cross-sectional geometries.

In some examples, the engagement end of the delivery device has a yield strength ranging between 175,000 psi and 250,000 psi, and in other examples, the engagement end of the delivery device has a yield strength is 220,022 psi.

Another approach is a fastening system. The fastening system includes a solid, monolithic shaft member having an engagement end. The engagement end has a proximal end and a distal end. The proximal end has a first cross-sectional geometry, and the distal end has a second cross-sectional geometry. The first cross-sectional geometry of the proximal end is different from the second cross-sectional geometry of the distal end. The cross-sectional geometry of the distal end transitions to the cross-sectional geometry of the proximal end along a longitudinal axis of the solid, monolithic shaft member. The transition provides a gradual, blending, continuously transitioning cross-sectional geometry along the entire length of the longitudinal axis of the engagement end of the solid, monolithic shaft member. The fastener system includes a fastener defining a longitudinal cavity of substantially the same shape as the cross-sectional geometry of at least one of the proximal end or the distal end of the engagement end of the solid, monolithic shaft.

In some examples, the cross-sectional geometry of the distal end is in a shape of at least one of a triangle, a square, a rectangle, a hex, a circle, an ellipse, a cross, and a torx. In some examples, the cross-sectional geometry of the proximal end is in a shape of at least one of a triangle, a square, a rectangle, a hex, a circle, an ellipse, a cross, and a torx. In other examples, the engagement end of the solid, monolithic shaft member includes no abrupt transitions in cross-sectional geometries along the longitudinal axis.

In some examples, the longitudinal cavity of the fastener provides a blending, continuously transitioning cross-sectional geometry along the longitudinal axis adapted for receiving the blending, continuously transitioning cross-sectional geometry of the engagement end of the solid, monolithic shaft. In some examples, the longitudinal cavity includes at least two different cross-sectional geometries along the longitudinal axis.

Another approach is a fastener for securing a suture. The fastener includes a body member having an exterior surface and defining an interior cavity. The exterior surface includes a fixation element; and the interior cavity includes a longitudinal cavity having a blending, continuously transitioning cross-sectional geometry along the longitudinal axis of the body member. In some examples, the longitudinal cavity includes at least two different cross-sectional geometries. In some examples, the longitudinal cavity is adapted for receiving an engagement end of a drive shaft having a cross-sectional geometry of substantially the same shape as the longitudinal cavity. In some examples, the exterior surface of the fastener further includes a retention element.

The blended shaft drive and fastening system described herein provides one or more of the following advantages. For example, one advantage of the blended shaft drive and fastening system is that the blended shaft drive allows for the application of increased torsional strength during fastener delivery, thereby enabling the blended shaft drive to secure a fastener without breaking and thereby reducing costs and health risks related to removing and replacing broken shaft and fastener assemblies from a patient undergoing arthroscopic surgery. Another advantage of the technology is that the blended shaft drive allows for reduced fastener size (i.e., reduced overall fastener implant size), thereby decreasing the manufacturing cost for the technology by reducing materials, improving fastener deployment in low clearance areas, and/or minimizing physical trauma to a recipient of the fastener. Another advantage of the technology is that the blended shaft drive allows for greater fixation strength of the mating fastener (e.g., less implant volume dedicated to applying torque allows for greater implant volume dedicated to fixation strength), thereby improving likelihood of fastener retention while reducing the overall cost and physical trauma to a recipient.

Other aspects and advantages of the current technology will become apparent from the following detailed description, taken in conjunction with the accompanying drawings, illustrating the principles of the technology by way of example only.

BRIEF DESCRIPTION OF THE DRAWINGS

The foregoing features of various examples of the technology will be more readily understood by reference to the following detailed descriptions in the accompanying drawings, in which:

FIG. 1C is a schematic illustration of a top perspective exploded view of a portion of the fastening system, according to the illustrative example of FIG. 1A;

FIG. 1D is a schematic illustration of a bottom perspective exploded view of a portion of the fastening system, according to the illustrative example of FIG. 1A;

FIG. 1E is a schematic illustration of a top view of an assembled portion of the fastening system, according to the illustrative example of FIG. 1A;

DETAILED DESCRIPTION

The blended shaft drive includes components that enable the reliable affixation of compact fasteners requiring secure placement in low clearance and/or limited access areas. For example, one use of the blended shaft drive is for securing a device (anchor/fastener/suture) that connects tendon to bone without causing a patient unnecessary physical trauma otherwise caused by invasive arthroscopic procedures. Because tendons absorb and impart strong forces, the device must affix such tendons securely to bone to enable successful healing. In this example, secure affixation is achieved by a system of an anchor and fastener, a suture, and the blended shaft drive that deploys the fastener within an anchor for securing the suture attached to a tendon. Compared to legacy drive tools, the blended shaft drive is relatively narrow for deploying a compact fastener that requires minimal clearance and a relatively small area footprint in the bone. Because the blended shaft geometry has no abrupt transitions, the relatively narrow blended shaft drive withstands high torque forces (at least 3 in-lbf) without breaking/failure.

Figures 1A, 1B:
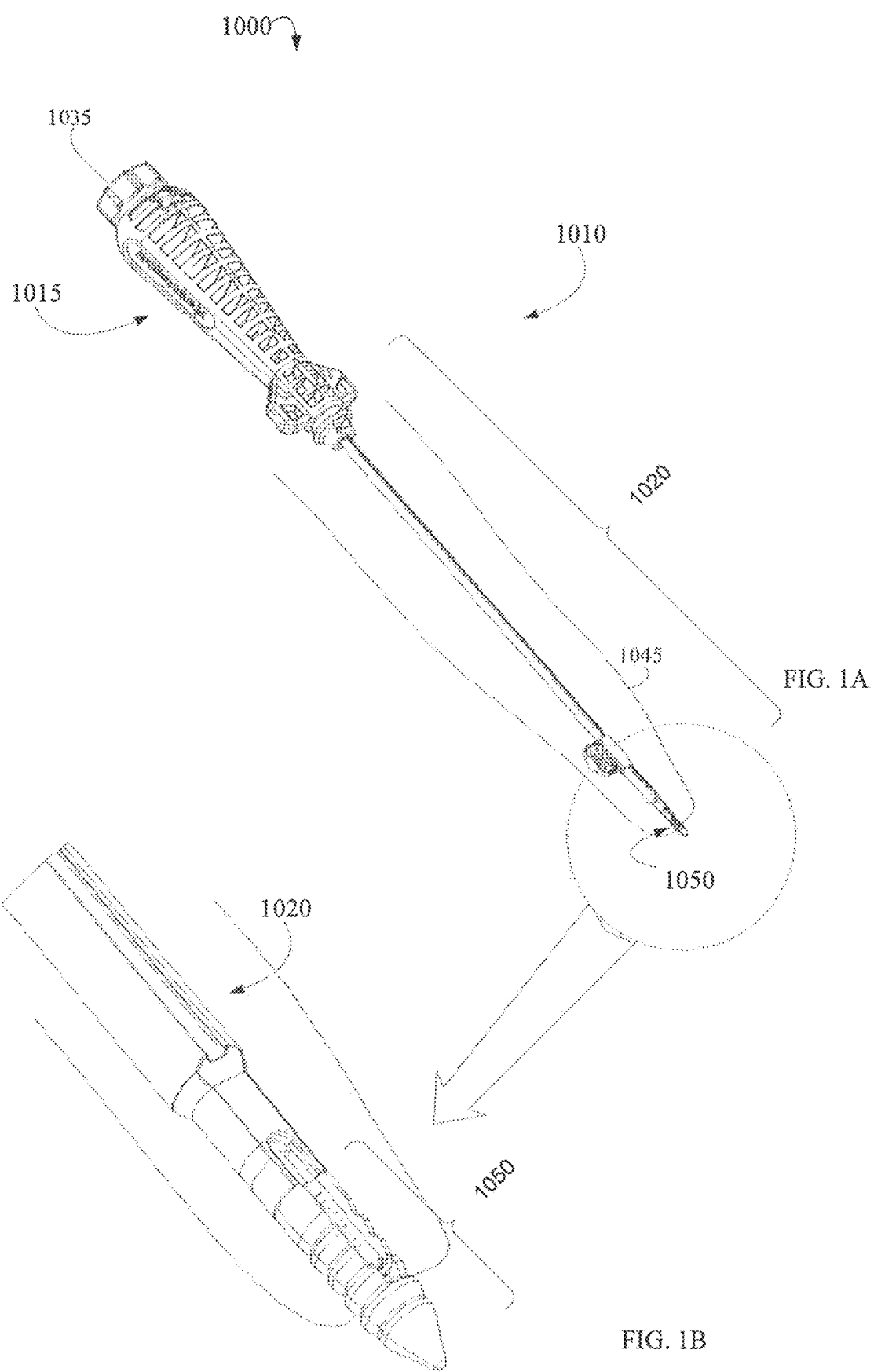
FIG. 1A is a schematic illustration of a perspective view of a fastening system, according to an illustrative example.
FIG. 1B is an enlarged bottom perspective view of a portion of the fastening system, according to the illustrative example of FIG. 1A.

FIGS. 1A through 1E depict an example of a fastening system 1000 including a high strength delivery device 1010 and a two part footprint anchor 1050. FIG. 1A illustrates the assembled components of the fastening system 1000. FIG. 1B shows a exploded enlarged portion of the fastening system 1000 of FIG. 1A. FIGS. 1C and 1D show exploded perspective views of the exploded portion of FIG. 1B. FIG. 1E shows an example of an enlarged schematic top view of assembled components of the fastening system 1000.

The delivery device 1010 includes an insertion handle 1015 and a two-part insertion shaft 1020 having a hollow outer shaft 1030 surrounding an inner, solid, monolithic shaft member 1025. The solid, monolithic shaft member 1025 is adapted for applying torque to an engaged fastener 1055. In some examples, the fastener 1055 requires placement within a receiving cavity of an outer body 1060 for securing a suture 1045 therebetween. The outer shaft 1030 engages with the outer body 1060. For example, the delivery device 1000 could be one for engaging, delivering, and securing a suture fixation fastening system for use in arthroscopic procedures involving securing tissue to bone. As some examples, the delivery device 1010 could be one for engaging, delivering and securing a fastener in any low-clearance assembly, such as those forming components of aircraft, automobiles, and bicycles, all of which require high torque fasteners in densely populated areas.

With regard to the example of a suture fixation fastening system 1000, such a system requires application of high torque on the fastener 1055 to secure a suture 1045 against the outer body 1060, which is securely driven into a bore formed in a bone 1070. The two-part footprint anchor 1050 thereby enables attachment of tissue (e.g., a tendon) to bone. Turning a torque limiter knob 1035 at the top of the inserter handle 1015 transfers torque to the solid monolithic shaft member 1025. The application of torque limiter knob 1035 enables the solid, monolithic shaft member 1025 to secure a fastener 1055 within the outer body 1060 without over tensioning the fastener 1055. The delivery device 1010 therefore secures strong tendon tissue to bone without the solid monolithic shaft member 1025 breaking/failing under the application of torsion force. This advantageously reduces costs and time otherwise associated with removing and replacing an assembly of the broken solid, monolithic shaft member 1025, the fastener 1055 and the suture 1045 from patients during surgery. Withstanding high torque forces enables the delivery device 1000 to deliver the fastener 1055 reliably, therefore decreasing the risks associated with prolonged surgery. The solid, monolithic shaft member 1025 also allows for reduced fastener size (i.e., reduced overall fastener implant size), thereby decreasing the manufacturing cost for the technology by reducing materials, improving fastener deployment in low clearance areas, and/or minimizing physical trauma to a recipient of the two part footprint anchor 1050. The solid, monolithic shaft member 1025 allows for greater fixation strength of the mating fastener 1055 (e.g., less implant volume dedicated to applying torque allows for greater implant volume dedicated to fixation strength), thereby improving the likelihood of fastener 1055 retention while reducing the overall cost of manufacture of the fastening system 1000.

Figure 2:
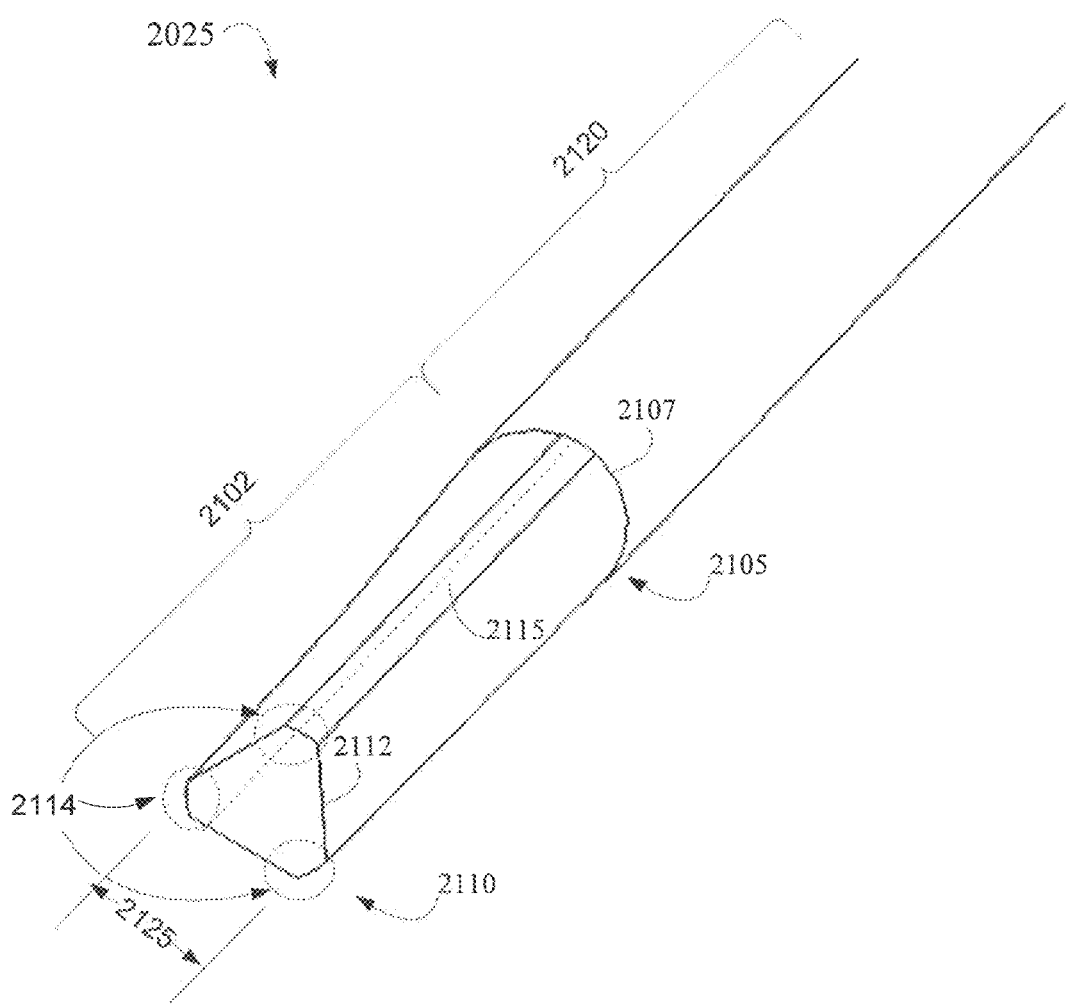
FIG. 2 is a schematic illustration of a perspective view of a blended shaft drive, according to an illustrative example.

FIG. 2 depicts a portion of an exemplary delivery device (e.g., delivery device 1010 of FIG. 1A), which includes a solid, monolithic shaft member 2025 having an engagement end 2102 for driving a fastener (e.g. fastener 3255 of FIG.

3A). In some examples, the solid, monolithic shaft member 2025 is manufactured from a single, solid piece of stock (e.g., surgical steel, composite, etc.). The solid, monolithic shaft member 2025 can be, for example, a unitary, single-component body having no cavity therein. The engagement end 2102 of the solid, monolithic shaft member 2025 has a proximal end 2105 and a distal end 2110 for engaging with the fastener 3255. The proximal end 2105 has a first cross-sectional geometry 2107 and the distal end 2110 end has a second cross-sectional geometry 2112. The first cross-sectional geometry 2107 of the proximal end 2105 is different from the second cross-sectional geometry 2112 of the distal end 2110. As illustrated in FIG. 2, the first cross-section geometry 2107 of the proximal end 2105 is a circle and the second cross-section geometry 2112 of the distal end 2110 is a triangle with flattened corners 2114. The flattened corners 2114 can prevent any concentrated, localized applications of force that would create potential modes of failure. Sharp corners on an engagement end can lead to potential cracking and/or fatiguing of a mated fastener during application of torque, thereby causing health risks and trauma associated with prolonging surgery to remove and replace a fastener and any deployed suture which has already been attached to the tissue requiring affixation to bone.

The second cross-sectional geometry 2112 of the distal end 2110 transitions to the first cross-sectional geometry 2107 of the proximal end 2105 along a longitudinal axis 2115 of the engagement end 2102 of the solid, monolithic shaft member 2025. The transition provides a gradual, blending, continuously transitioning cross-sectional geometry along the entire length of the longitudinal axis 2115 of the engagement end 2102 of the solid, monolithic shaft member 2025. The first cross-sectional geometry 2107 of the proximal end 2105 therefore transitions into the second cross-sectional geometry 2112 of the distal end 2110 without any abrupt transitions that would trigger the accumulation of stress risers (i.e., areas of concentrated stress) that could lead to catastrophic yield or breakage. A rapid transition in geometry (i.e., a geometric discontinuity) weakens an object because force is not evenly distributed over the object. Instead, localized increases in stress occur when an abrupt transition in geometry occurs. By smoothly and progressively transitioning from one cross-sectional geometry to another along the longitudinal axis 2115 of the engagement end 2102, the solid, monolithic shaft 2025 eliminates rapid transitions, such as tapers and undercuts, and therefore eliminates rapid physical changes that induce stress risers. The smooth and progressive transition advantageously enables the application of high torque without the risk of breaking apart the solid, monolithic shaft 2025 and requiring costly and risky extraction and replacement of the fastener 3255 and suture (not shown).

In some examples, the cross-sectional geometry of the distal end 2110 is in a shape of at least one of a triangle, a square, a rectangle, a hex, a circle, an ellipse, a cross, and a torx, for example. In some examples, the cross-sectional geometry of the proximal end 2105 is in a shape of at least one of a triangle, a square, a rectangle, a hex, a circle, an ellipse, a cross, and a torx, for example. In other examples, the cross-sectional geometry of the distal end 2105 is in a shape of a polygon, the sides thereof providing sufficient contact with a fastener (e.g. 3255 of FIG. 3A) such that an application of torque on the solid, monolithic shaft 2025 drives the engaged fastener 3255. In yet some examples, a torque application end 2120 includes at least a third cross-sectional geometry (not shown). In examples, any number of cross-sectional geometries is contemplated such that the transitions between geometries are progressive and no abrupt transitions in geometry exist. Although the distal end 2110 and the proximal end 2105 are described as being one of a listed shape, the distal end 2110 and/or the proximal end 2105 can be any shape and/or any combination of shapes (e.g., square to diamond, torx to circle, rectangle to octagon, etc.)

In some examples, the cross-sectional geometry of at least one of the proximal end 2105 or the distal end 2110 has a shape adapted to mate with a fastener cavity (e.g. 3215 of FIG. 3A) of substantially the same shape. In some examples, the fastener cavity provides a blending, continuously transitioning cross-sectional geometry along the longitudinal axis (e.g. 3217 of FIGS. 3B, 3C and 3D) of the cavity adapted for receiving the blending, continuously transitioning cross-sectional geometry of the engagement end 2102 of the solid, monolithic shaft 2025. In other examples, the fastener cavity includes at least two different cross-sectional geometries (e.g., square and diamond, torx and circle, rectangle and octagon, etc.).

Figure 3A:
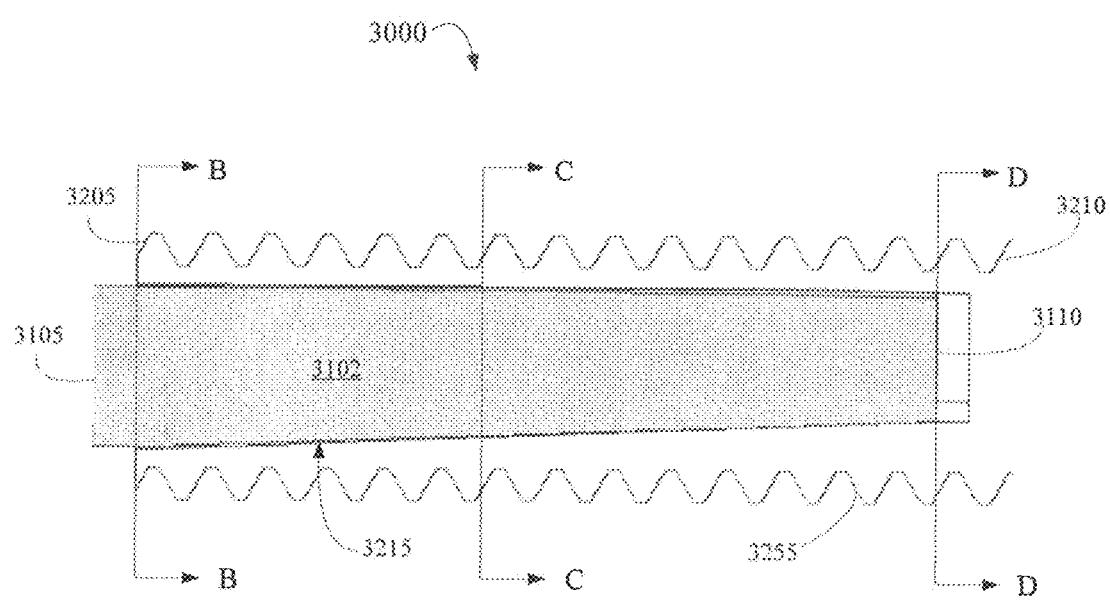
FIG. 3A is a schematic illustration of a cross-sectional side view of a blended shaft drive mated with a fastener, according to an illustrative example.

The engagement end 2102 of the solid, monolithic shaft 2025 of FIG. 2 inserts into a fastener cavity (e.g. 3215 of FIG. 3A). As shown in the exemplary fastener 3255 and engagement end 2102 assemblies of FIGS. 3A through 3D, the fastener 3255 is sized and shaped to accommodate the blending, continuously transitioning cross-sectional geometry of the engagement end 2102 so that fastener 3255 and engagement end 2102 are mated in a press fit or substantially press fit configuration. The engagement end 2102 outside dimension 2125 is substantially equal to or less than the diameter of the fastener cavity 3215. In some examples, the cavity 3215 is sized to accommodate the blending, continuously transitioning cross-sectional geometry of the engagement end 2102 in a press fit, or substantially press fit, configuration such that the engagement end 2102 can deliver fastener 3255 while still enabling removal of the solid, monolithic shaft 2025 from the cavity 3215 following secured placement of the fastener 3255. This enables the successful application of high torque (e.g., 3 in-lbf, 4 in-lbf, etc.) required to properly secure components, e.g. a sutured tendon to bone, while preventing the development of stress risers along the blending, continuously transitioning cross-sectional geometry of the engagement end 2102. By preventing stress risers, the solid, monolithic shaft 2025 reliably deploys a fastener 3255 without breaking off in the fastener. Preventing such breakage eliminates the health risks and costs associated with removal and replacement of the faster and suture.

Figure 3B:
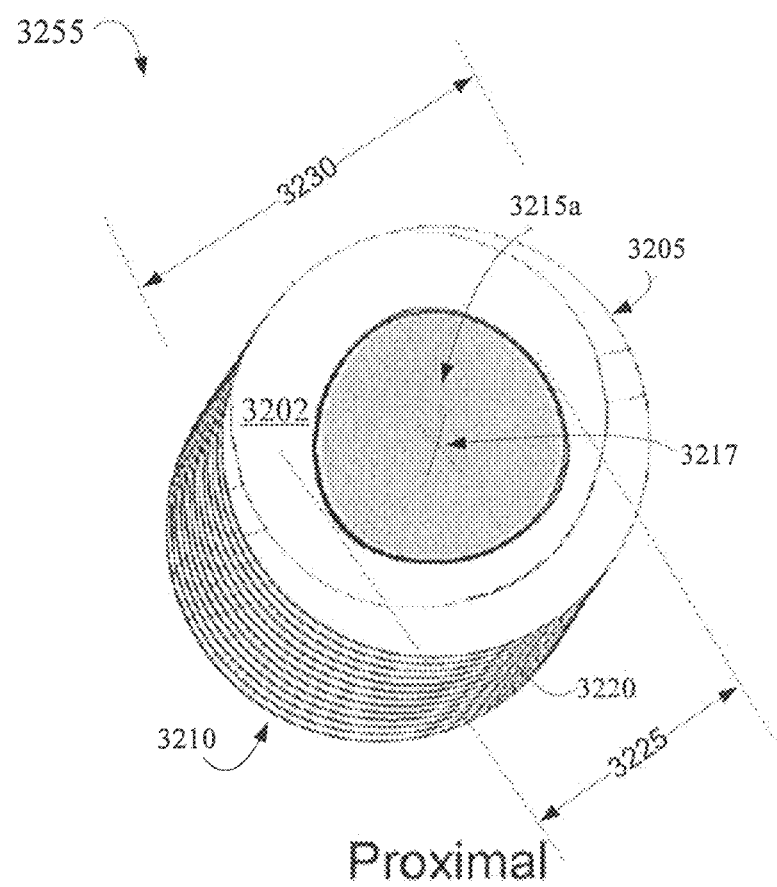
FIG. 3B is a schematic illustration of a perspective end view of the example of FIG. 3A cross-sectioned along line B-B.
Figure 3C:
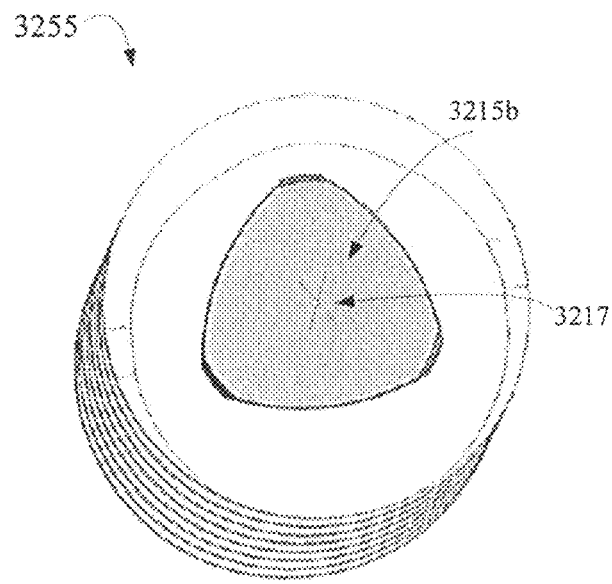
FIG. 3C is a schematic illustration of a perspective end view of the example of FIG. 3A cross-sectioned along line C-C.
Figure 3D:
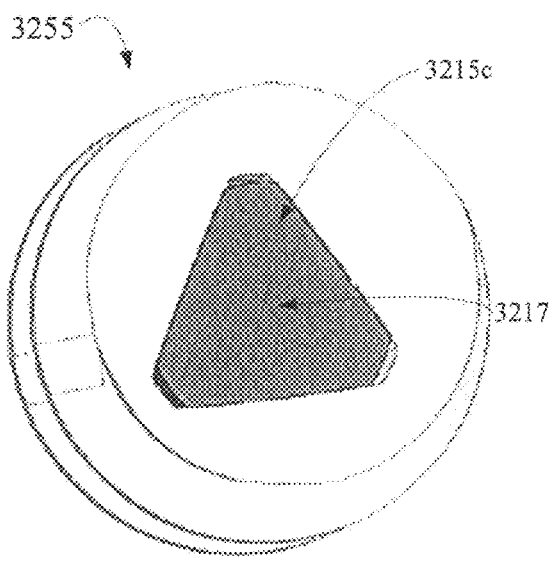
FIG. 3D is a schematic illustration of a perspective end view of the example of FIG. 3A cross-sectioned along line D-D.

FIGS. 3B, 3C, and 3D are cross-sectional views of the exemplary fastener-shaft assembly 3000 of FIG. 3A cross-sectioned along lines B-B, C-C, and D-D respectively. As illustrated in FIG. 3B, the fastener cavity 3215 has a substantially circular cross-sectional shape 3215*a* at a proximal end 3205 of the fastener 3255 (i.e., point (B-B) along the longitudinal axis 3217). As illustrated in FIG. 3C, the fastener cavity 3215 has a hybrid circle-triangle cross-sectional shape 3215*b* at a midway point (C-C) along the longitudinal axis 3217, and as illustrated in FIG. 3D, the fastener cavity 3215 has a triangular cross-sectional shape 3215*c* at a distal end 3210 of the fastener 3255 (i.e., a point (D-D) along the longitudinal axis 3217).

Figure 4:
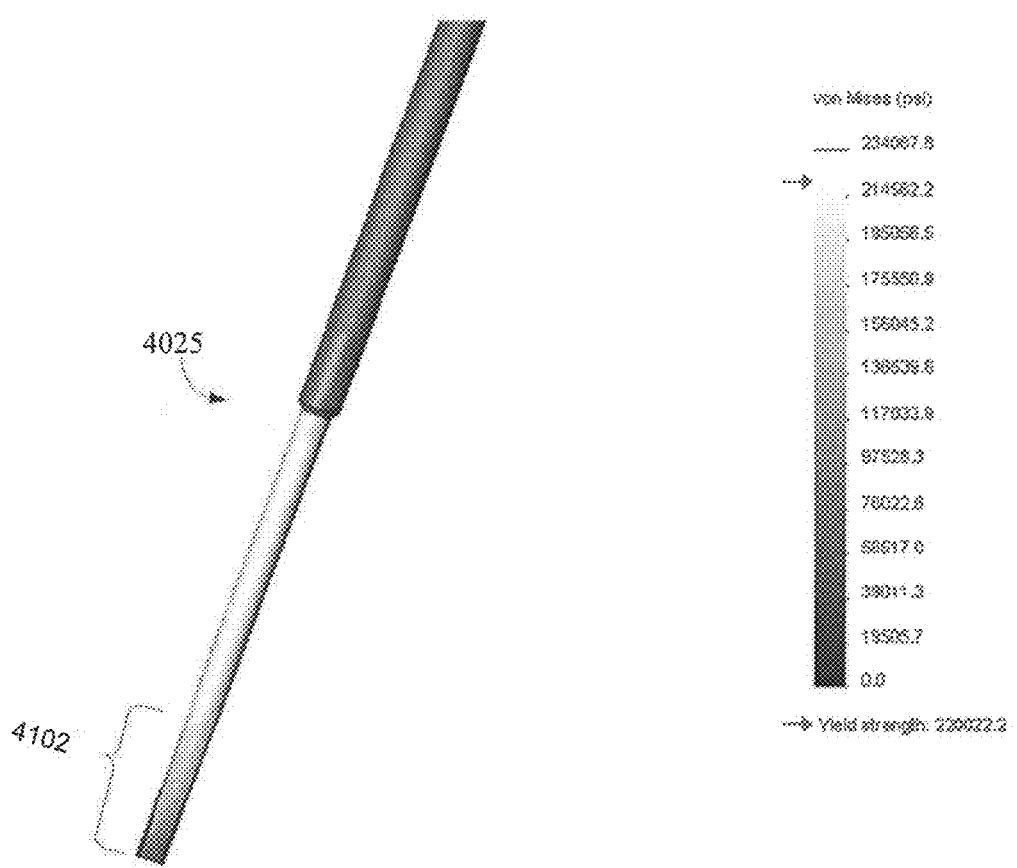
FIG. 4 is a schematic illustration of a perspective view of a delivery device exhibiting stress concentrations under load, according to an illustrative example.

As depicted in FIG. 4, in some examples, the engagement end 4102 of a solid, monolithic shaft 4025 has a yield strength ranging between 175,000 psi and 250,000 psi, and in other examples, the engagement end 4102 has a yield strength of 220,022 psi. This range of yield strengths is three times greater than a legacy drive tool 5025 depicted in FIG.

Figure 5:
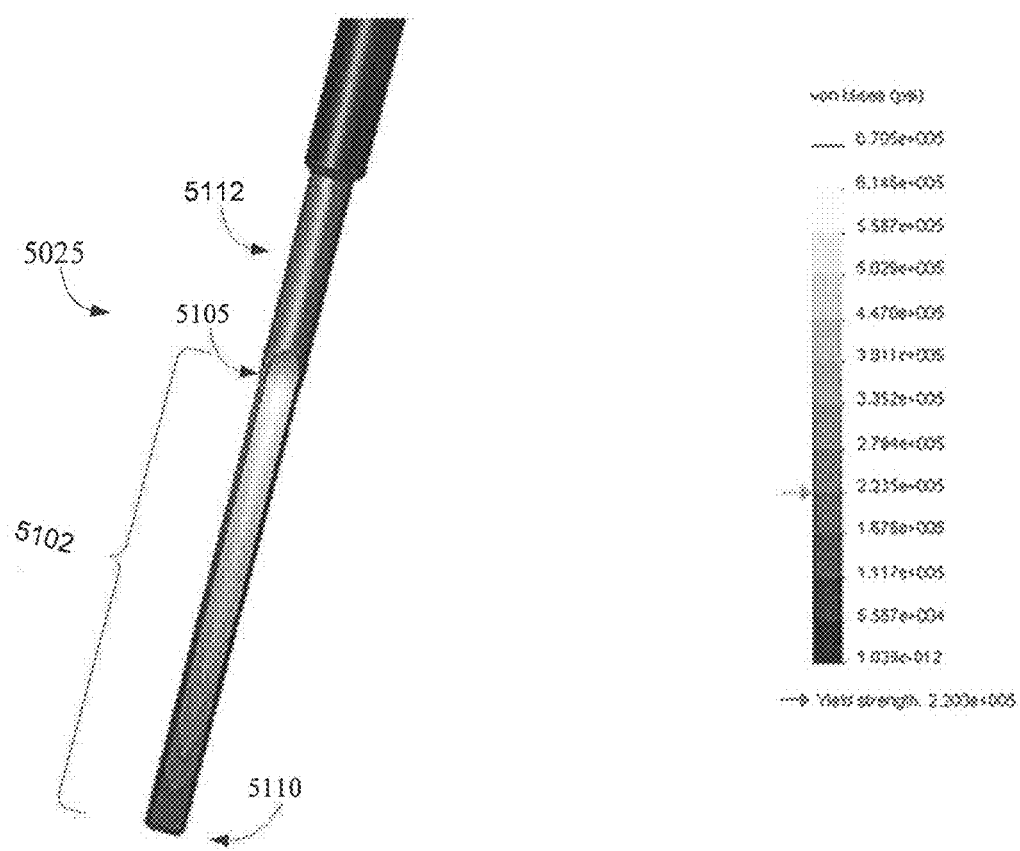
FIG. 5 is a schematic illustration of a perspective view of a prior art delivery device exhibiting stress concentrations under load.

5 that incorporates an engagement end 5102 of continuous cross-sectional geometry that transitions rapidly at a taper or undercut 5105, for example, into a larger geometry. Such a legacy drive tool 5025 typically fails under a torque load of 3 in-lbf, the torque required to secure a suture within an arthroscopic fastening anchor system comprising a fastener (not shown) mated to an anchor (not shown) with a suture secured therebetween. As FIG. 5 indicates, a stress riser occurs at the transition point 5110 between the engagement end 5102 and the larger diameter portion 5112 of the drive tool 5025, and adjacent the rapid transition in geometry occurring at the taper 5105.

By eliminating rapid transitions in geometry, the solid, monolithic shaft 4025 addresses the issue of catastrophic failure that would lead to the engagement end 4102 snapping off of the solid, monolithic shaft 4025 during deployment of a fastener (not shown). As the example of FIG. 4 indicates, the solid monolithic shaft 4025 withstands 3 in-lbf of torque without exhibiting concentrated stress risers that would lead to catastrophic failure. The solid, monolithic shaft 4025 therefore enables the delivery and fastening of extremely small fasteners without the solid, monolithic shaft 4025 breaking under torque load required, for example, for proper suture fixation during arthroscopic surgery.

In some examples, such as the example of related FIGS. 2 and 3B, the outside dimension 2125 of the distal end 2110 of engagement end 2102 is no more than 1.2 mm and the outside diameter 3230 of the fastener 3255 is no more than 2 mm. In this example, the engagement end 2102 and fastener are no more than 10 mm long each as measured along longitudinal axes 2115 and 3217. In this example, the delivery device comprising the engagement end 2102 and torque application end 120 is 16 inches long. Eliminating abrupt transitions in geometry therefore enables a solid, monolithic shaft 2025 to deliver a micro-scale fastener 3255 in a low clearance area and apply sufficient torque (e.g., 3 in-lbf) to secure sutures 1045 without catastrophic breakage of the delivery device (e.g., 1010 of FIG. 1A). The progressive transition in cross-sectional geometry allows for increased torsional strength of the delivery device and decreased fastener diameter.

Another example is a fastening system 1000 including a solid, monolithic shaft member 1025 and a fastener 1055. In some examples, the solid, monolithic shaft member 1025 has an engagement end 2102, and the engagement end 2102 has a proximal end 2105 and a distal end 2110. The proximal end 2105 has a first cross-sectional geometry 2107 and the distal end 2110 has a second cross-sectional geometry 2112, and the first cross-sectional geometry 2107 of the proximal end 2105 is different from the second cross-sectional geometry 2112 of the distal end 2110. The second cross-sectional geometry 2112 of the distal end 2110 transitions to the cross-sectional geometry 2107 of the proximal end 2105 along a longitudinal axis of the solid, monolithic shaft member 2025 providing a gradual, blending, continuously transitioning cross-sectional geometry along the entire length of the longitudinal axis 2115 of the engagement end 2102 of the solid, monolithic shaft member 2025. In examples, the fastener system includes a fastener 3255 defining a longitudinal cavity 3215 of substantially the same shape as the cross-sectional geometry of at least one of the proximal end 2105 or the distal end 2110 of the engagement end 2102 of the solid, monolithic shaft member 1025.

In some examples, the second cross-sectional geometry 2112 of the distal end 2110 is in a shape of at least one of a triangle, a square, a rectangle, a hex, a circle, an ellipse, a cross, and a torx. In some examples, the cross-sectional geometry of the proximal end 2105 is in a shape of at least one of a triangle, a square, a rectangle, a hex, a circle, an ellipse, a cross, and a torx. In other examples, the engagement end 2102 of the solid, monolithic shaft member 2025 includes no abrupt transitions in cross-sectional geometries along the longitudinal axis 2115.

As depicted in the illustrative examples of FIGS. 3A through 3D, the longitudinal cavity 3215 of the fastener 3255 provides a blending, continuously transitioning cross-sectional geometry along the longitudinal axis 3217 adapted for receiving the blending, continuously transitioning cross-sectional geometry of the engagement end 2102 of the solid, monolithic shaft 2025. In examples, the longitudinal cavity 3215 includes at least two different cross-sectional geometries along the longitudinal axis 3217. In some examples, the cavity 3215 is sized to accommodate the blending, continuously transitioning cross-sectional geometry of the engagement end 2102 of FIG. 2 in a press fit or substantially press fit configuration such that the engagement end 2102 can deliver fastener 3255 while still enabling removal of the solid, monolithic shaft 2025 from the cavity 3215 following securing the fastener 3255.

Figure 6:
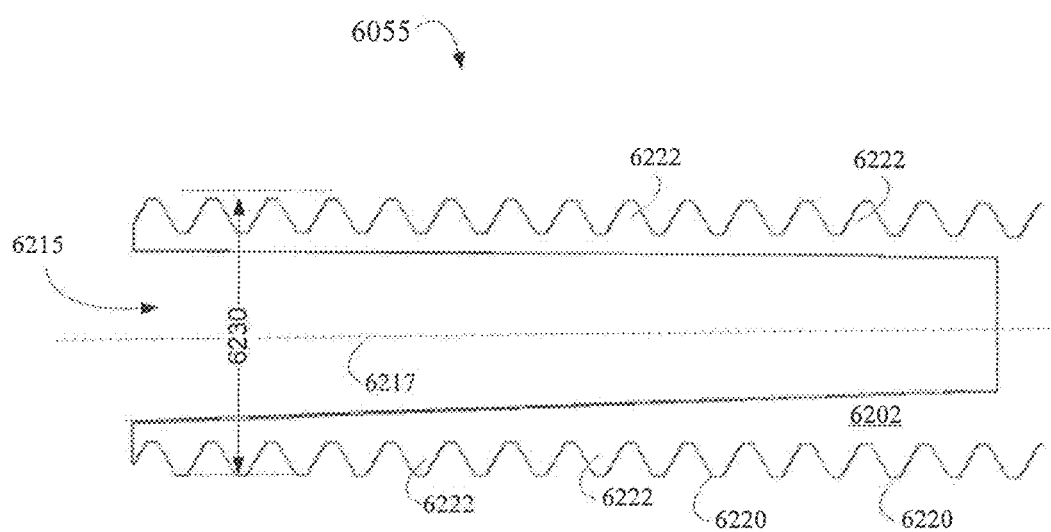
FIG. 6 is a schematic illustration of a cross-sectional side view of a fastener, according to an illustrative example.

Illustrated in FIG. 6 is an exemplary fastener 6055 for securing a suture including a body member 6202 having an exterior surface 6220 and defining an interior cavity 6215. The exterior surface 6220 includes a fixation element 6222. In one example, the fixation element 6222 includes threads or barbs and threads; however it is possible that the fixation element 6222 may include only barbs. The interior cavity 6215 of the exemplary fastener 6055 includes a longitudinal cavity having a blending, continuously transitioning cross-sectional geometry along the longitudinal axis 6217 of the body member 6202. In some examples, the longitudinal cavity 6215 includes at least two different cross-sectional geometries, as depicted in the illustrative examples of FIGS. 3A through 3D. In the illustrated example, the cross-sectional geometry of the longitudinal cavity 3215 progressively transitions from a circle-shaped cavity 3215a to a triangle shaped cavity 3215c. In some examples, such as that of FIGS. 2 through 3D, the longitudinal cavity 3215 is adapted for receiving an engagement end 2102 of a solid, monolithic shaft 2025 having a cross-sectional geometry of substantially the same shape as the longitudinal cavity 3215.

In some examples, such as that of FIG. 6, the exterior surface 6220 of the fastener 6055 further includes at least one retention element (not shown). The retention element may be threads or barbs or a combination of threads and barbs, for example. For the purposes of this technology, the retention element includes threads or barbs and threads; however it is possible that the retention element may include only barbs. For example, two thirds of the exterior surface (e.g., as measured along the longitudinal axis) can be covered in a fixation element 6222 of engagement threads and the remaining third can comprise a retention element of one or more retention barbs. In any example, the lack of abrupt geometric transition along the solid, monolithic shaft (e.g. 2025 of FIG. 2) of the delivery device (e.g. 1010 of FIG. 1A) enables reduction in size of the deployed fastener 6055. Specifically, the gradual transition along the solid, monolithic shaft allows for a reduction in outside diameter 6230 of the fastener 6055. This thereby allows for greater fixation strength because less volume of the fastener 6055 is dedicated to applying torque and a greater volume is dedicated to fixation strength (e.g., deeper threads).

Comprise, include, and/or plural forms of each are open ended and include the listed parts and can include additional parts that are not listed. And/or is open ended and includes one or more of the listed parts and combinations of the listed parts.

One skilled in the art will realize the technology may be embodied in other specific forms without departing from the spirit or essential characteristics thereof. The foregoing examples are therefore to be considered in all respects illustrative rather than limiting of the technology described herein. Scope of the technology is thus indicated by the appended claims, rather than by the foregoing description, and all changes that come within the meaning and range of equivalency of the claims are therefore intended to be embraced therein.

I claim:

1. A fastening system, comprising:
   a) a delivery device, comprising:
      a solid, monolithic shaft member having an engagement end configured and dimensioned for engaging with a longitudinal cavity of a fastener, the engagement end having a proximal end and a distal end,
      wherein the engagement end defines a gradual blended continuous transition between a first cross-sectional geometry at the proximal end and a second cross-sectional geometry at the distal end different than the first cross-sectional geometry,
      wherein the gradual blended continuous transition is further characterized by a gradual blended continuous tapering of a diameter of the engagement end between the proximal end and the distal end of the engagement end, and
      wherein a number of sides or lobes of the first cross-sectional geometry are different from a number of sides or lobes of the second cross-sectional geometry; and
   b) a fastener defining a longitudinal cavity of substantially the same shape as the engagement end of the shaft member of the delivery device;
   wherein the second cross-sectional geometry is in a shape of a triangle with flattened corners.

2. The fastening system of claim 1, wherein the first cross-sectional geometry is substantially circular.

3. The fastening system of claim 1, wherein the engagement end of the solid, monolithic shaft member comprises no abrupt transitions in cross-sectional geometries along the longitudinal axis.

4. The fastening system of claim 1, wherein the longitudinal cavity provides a blending, continuously transitioning cross-sectional geometry along the longitudinal axis adapted for receiving the blending, continuously transitioning cross-sectional geometry of the engagement end of the solid, monolithic shaft member.

5. A fastening system, comprising:
   a) a delivery device, comprising:
      a solid, monolithic shaft member having an engagement end configured and dimensioned for engaging with a longitudinal cavity of a fastener, the engagement end having a proximal end and a distal end, wherein the engagement end defines a gradual blended continuous transition between a substantially circular cross-sectional geometry of the shaft member extending proximally from the proximal end of the engagement end and a non-circular cross-sectional geometry at the distal end different from the substantially circular cross-sectional geometry of the shaft member; and
   b) a fastener defining a longitudinal cavity of substantially the same shape as the engagement end of the shaft member of the delivery device;
   wherein the delivery device further includes an outer shaft surrounding the solid, monolithic shaft member, the outer shaft being configured to engage with an outer body of an anchor while the solid, monolithic shaft member engages with the longitudinal cavity of the fastener, whereby the outer shaft is configured to hold the outer body in place while the monolithic shaft applies a torque to the fastener.

6. The fastening system of claim 5, wherein the longitudinal cavity provides a blending, continuously transitioning cross-sectional geometry along the longitudinal axis adapted for receiving the blending, continuously transitioning cross-sectional geometry of the engagement end of the solid, monolithic shaft member.

7. The fastening system of claim 5, wherein the delivery device further includes a torque limitation mechanism for preventing over tensioning of the fastener.

* * * * *